United States Patent [19]

Inaba

[11] 3,968,342
[45] July 6, 1976

[54] MOISTURE RESPONSIVE SYSTEM FOR REMOVING CONDENSATION

[75] Inventor: Hiroshi Inaba, Saitama, Japan
[73] Assignee: Central Glass Co., Ltd., Japan
[22] Filed: July 24, 1972
[21] Appl. No.: 274,611

[30] Foreign Application Priority Data
July 31, 1971 Japan.................................. 46-57804

[52] U.S. Cl. .............................. 219/203; 219/522; 317/DIG. 3
[51] Int. Cl.² ........................................ B60L 1/02
[58] Field of Search............................ 219/203, 522; 317/DIG. 3

[56] References Cited
FOREIGN PATENTS OR APPLICATIONS
884,967    12/1961    United Kingdom................ 219/203

*Primary Examiner*—R. N. Envall, Jr.
*Attorney, Agent, or Firm*—Lane, Aitken, Dunner & Ziems

[57] ABSTRACT

A device for controlling electric current flowing through a conductor-coated, condensation-free transparent glass sheet in response to the presence of moisture on the surface of the sheet. Moisture-detecting electrodes forming part of an oscillator are attached to the surface of the sheet and receive an AC voltage developed within the oscillator. The electrical resistance between the electrodes changes in response to the amount of moisture and alters the level of output from an oscillator. A relay circuit is controlled by the oscillator output to switch a power supply circuit on and off, thereby controlling the current flowing through the glass sheet.

2 Claims, 1 Drawing Figure

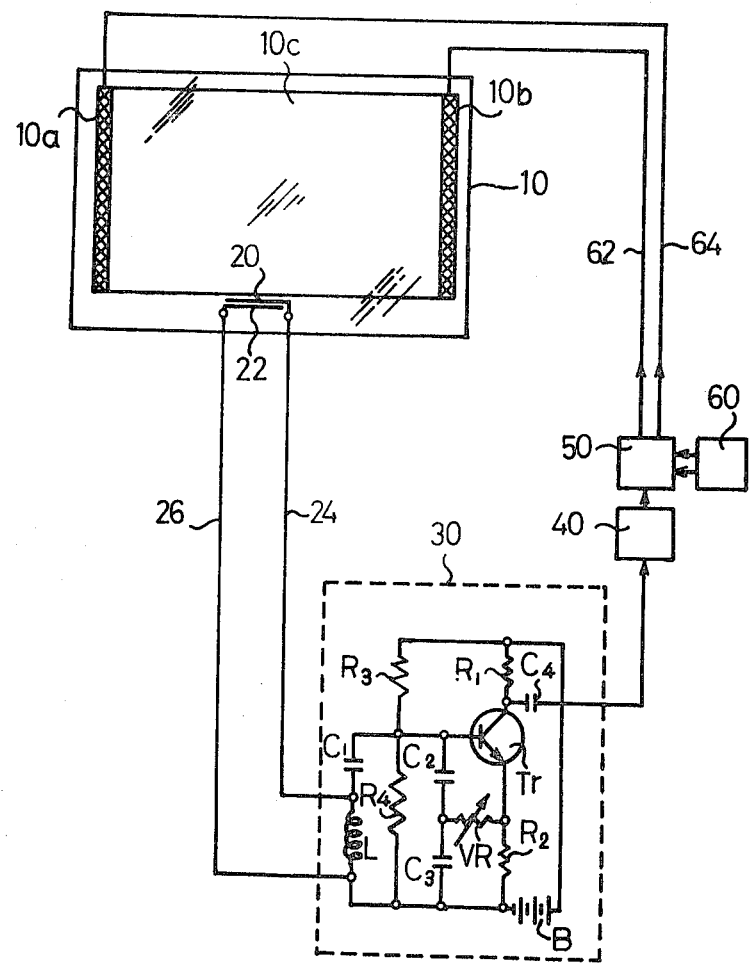

MOISTURE RESPONSIVE SYSTEM FOR REMOVING CONDENSATION

BACKGROUND OF THE INVENTION

The invention relates to a device for controlling electric current flowing through a condensation-free transparent glass sheet to eliminate vapor condensation thereon by means of electric heating elements.

Condensation formed on the glass window of an automobile obscures the driver's view and hampers driving. To solve this problem, it has been the practice to coat the glass window with a transparent conductive film or a plurality of conductive lines or stripes which serve as heating elements. The same measures are also taken for a similar problem experienced with refrigerators. The on-off control of the power supply for conductor-coated glass sheets is usually performed by manual switches or automatic timer switches. In the former, however, the switching operation is troublesome and tends to involve excessive power consumption due to neglect by the operator. Likewise, in the latter, it is hard to set the optimum operating period of the heating elements. Therefore, a considerable amount of power loss will result. There is another system in which a thermistor is attached to the surface of the glass sheet, so as to control the heater current in accordance with the detected temperature, and thereby maintain the glass sheet at a constant temperature. It is well known, however, that the dew point depends not only on ambient temperature but also on humidity. This gives rise to difficulties in achieving the optimum temperature setting for the thermistor. For these reasons, excessive power consumption necessarily results even in the thermistor — controlled system.

A pair of moisture-detecting electrodes attached to the surface of the glass sheet may be employed to turn the heater current on and off in response to variations in resistance caused by condensation. Thus, the heating can be controlled in accordance with the moisture or the degree of condensation on the surface of the glass sheet. Power consumption is minimized in this system. However, if a DC voltage is applied across the dewdetection electrodes, they tend to become corroded due to the ion transfer caused by the applied potential. This problem may be avoided by the use of corrosion-resistant materials of precious metals, e.g. platinum (Pt), gold (Au), palladium (Pd). These materials are costly, however, and differ from the materials ordinarily used for the heating elements, for example, a glass film containing silver powder baked to form stripes on the surface of the glass sheet or a transparent coating of tin oxide. Accordingly, separate steps are required for manufacture where the detecting electrodes are corrosion-resistant. The production process is simplified if the detecting electrodes and heating elements are made of the same materials.

SUMMARY OF THE INVENTION

It is therefore an object of the present invention to provide an arrangement for controlling electric current flowing through a conductor-coated, condensation-free transparent glass sheet in response to the level of moisture on the surface thereof so that power consumption is minimized.

Another object of this invention is to provide a control device of this kind, whose moisture-detecting electrodes are corrosion-free and may be made of any conductive metal.

Still another object of this invention is to provide a control device of this kind adapted to be energized by electric current from a battery and suited for use in an automobile.

In order to achieve these and other objects of the invention, moisture-detecting electrodes forming part of an oscillator are attached to the surface of the conductor-coated glass sheet and receive an AC voltage developed within the oscillator, so that the level of condensation formed on the surface may be translated into a change in electrical resistance between the electrodes to alter the output level of the oscillator. The oscillator output turns a relay circuit on and off to control the heater current for the glass sheet to eliminate condensation.

The use of an AC voltage for moisture-detection prevents the electrode corrosion which is otherwise caused by the transfer of metal ions from the electrodes, and which tends eventually to adversely affect their performance.

The control of the relay circuit by the oscillator output level varying in response to the electrical resistance between the detection electrodes renders the device highly responsive to the state of condensation in the vicinity of the detection electrodes.

One of the important advantages of the present invention is that the same oscillator circuit is used to detect a change in electrical resistance between the detection electrodes due to condensation and to apply AC voltage to the detection electrodes.

The arrangement of heating elements for use in conductor-coated, condensation-free glass sheets employed in this invention includes sheets coated with conductive film or a plurality of conductive stripes. Transparent conductive film is produced as by bringing a tin chloride solution into contact with a heated glass sheet, thereby decomposing said tin chloride, after which a film of tin oxide is deposited on the surface of the glass sheet. Conductive stripes are prepared by applying to a glass sheet stripes of paste consisting of silver powder and glass powder of low melting point, followed by baking at an elevated temperature.

The detecting electrodes are provided in the form of a pair of adjacent conductive stripes made of the same material or by atomizing a metal. To prevent electrolytic corrosion, a metal such as silver, nickel, aluminum or the like may be employed.

The condensation-free state of the conductor-coated glass sheet is achieved in the present invention by the novel combination of the moisture-detecting electrodes, oscillator and relay circuit. A preferred embodiment of the present invention will now be described referring to the accompanying drawing.

BRIEF DESCRIPTION OF THE DRAWING

The drawing shows a block and schematic circuit diagram of an embodiment of this invention.

DESCRIPTION OF THE PREFERRED EMBODIMENT

Referring to the drawing, a conductor-coated condensation-free glass sheet 10, which may be of any available type, has terminals 10a and 10b for connection to a power supply. A transparent conductive film 10c is applied to the surface between these terminals. At least one pair of moisture-detecting electrodes 20 and 22 are disposed at an arbitrary point on the surface, e.g. at a point below the film 10c. The detecting electrodes 20 and 22 may be in the form of two or more parallel stripes made of material identical to the transparent conductive film 10c which constitutes the heating element, said detecting electrodes being prepared together with said film. The electrodes 20 and 22 are connected to an oscillator 30 by leads 24 and 26, which are impressed with AC current developed between the ends of the coil L in the oscillating circuit including the oscillator 30.

It has been experimentally proved that the electrodes 20 and 22 remain free of corrosion if the applied AC voltage is at a frequency higher than 100 Hz. Therefore, the oscillator 30 is arranged to have an output frequency in that region. The oscillator may be of any type, although an LC oscillator is employed in the embodiment. The oscillator 30 has a transistor Tr, resistors $R_1$, $R_2$, $R_3$ and $R_4$, a variable resistor VR, capacitors $C_1$, $C_2$, $C_3$ and $C_4$, coil L, and power source B, coupled with each other in a conventional manner to form a Colpitts-type oscillating circuit. Capacitor $C_1$ blocks the DC component. The oscillation frequency is set at an arbitrary value, e.g. in the range of 0.1 – 100 kHz, by the appropriate choice of capacitance of capacitors $C_1$, $C_2$ and $Ck_3$ and the inductance of the coil L. An oscillating signal in this frequency range does not cause any interference to a radio receiver set installed in an automobile, even if the oscillator is placed close to the receiver set because the lower end of the broadcast band is about 500 kHz. Detection electrodes 20 and 22 are connected to the terminals of the coil L, while the output of the oscillator 30 is applied to a rectifier circuit 40 through a coupling capacitor $C_4$.

Electric current for the heating of the glass sheet 10 is supplied from a power source 60, which may be either an AC or DC power souce. When the glass sheet 10 is the windshield of an automobile, the power source 60 may be an automotive battery. The power source 60 is connected to the terminals 10a and 10b through a relay circuit 50 and leads 62 and 64.

In operation, the condensation of atmospheric moisture on the surface of the glass sheet 10 decreases the resistance between the electrodes 20 and 22. This in turn decreases the apparent impedance of the coil L coupled in parallel with the electrodes. This results in a decrease in the amplitude of the oscillator output. When condensation is absent through evaporation, resulting in an increased resistance, the apparent impedance of the coil L returns to the initial value to restore the maximum oscillator output. Relay circuit 50 is arranged to cut off the power supply circuit for the glass sheet 10 when the oscillator output reaches a near-maximum level, and to switch on the same circuit when the output has decreased to a level lower than a preset level.

As condensation begins to form on the surface of the glass sheet 10, the electrical resistance between the detection electrodes 20 and 22 decreases, resulting in a decrease in the apparent impedance of the coil L and consequently in the output of the oscillator 30.

This in turn results in the decrease in the DC output of the rectifier circuit 40, turning the relay circuit 50 on. Thus, the heater element on the glass sheet 10 is switched on to evaporate dew drops formed on the surface.

The progress of the evaporation results in an increase in the resistance between the electrodes 20 and 22, bringing the apparent impedance of the coil L back to the initial value and restoring the maximum or near-maximum oscillation level. Consequently, the DC output level at the rectifier 40 is raised to operate the relay circuit 50 to cut off the power supply circuit for the glass sheet 10.

In summary, the variation in resistance between the detection electrodes 20 and 22 dependent on the degree of condensation is translated into a change in the output level of the oscillator 30, which controls energization of the relay circuit 50 so as to turn the heating element power supply circuit on and off. This device ensures highly responsive on-off control for the heating element. Furthermore, the use of AC voltage instead of DC for moisture detection eliminates the possibility of corrosion of electrodes 20 and 22. This prevents changes in the contact resistance at these electrodes and eliminates the need for the use of corrosion-resistant materials, such as precious metals, rendering the manufacture less costly and less difficult. Further, for both generating the AC voltage which is applied to the detection electrodes and detecting the change in electrical resistance between the detection electrodes, the present invention is provided with only one oscillating circuit, separate circuits performing these two functions being unnecessary. Needless to say, the scope of the invention is not limited to the embodiment. Various modifications are possible within the scope of the invention defined in the appended claims.

I claim:

1. In moisture-responsive apparatus for removing vapor condensation from a transparent glass sheet having a heating element and electrical terminals, the improvement comprising:
    a pair of moisture-detecting electrodes mounted on said glass sheet;
    an oscillator incorporating said pair of electrodes as component parts thereof for applying an internally developed AC voltage to said electrodes, said electrodes being interconnected with said oscillator such that a change in electrical resistance between said electrodes causes a corresponding change in the output level of said oscillator; and
    a relay circuit operatively connected to said oscillator for switching a current supply to said heating element on and off in accordance with the output level of said oscillator.

2. In moisture-responsive apparatus for use in removing vapor condensation from a transparent glass sheet adapted for use as an automobile window having a heating element and electrical terminals, the improvement comprising:
    a pair of moisture-detecting electrodes mounted on said glass sheet;
    an LC oscillating circuit including a coil, capacitors, resistors and a transistor operatively interconnected, said coil being serially connected with one of said capacitors for blocking DC current, the terminals of said coil being respectively connected with said electrodes whereby a change in electrical resistance between said electrodes due to moisture causes a change in the AC voltage across said coil as well as a change in the level of the output of said oscillating circuit;
    a rectifier circuit for rectifying the output of said oscillating circuit; and
    a relay circuit operatively connected for energization by the output of said rectifier circuit to turn a supply of current to said heating element on and off.

* * * * *